United States Patent [19]

Hatter et al.

[11] 4,236,510

[45] Dec. 2, 1980

[54] ULTRASONIC TOOTH CLEANING APPARATUS

[76] Inventors: Edward E. Hatter, 31377 E. Nine Dr., Laguna Niguel, Calif. 92677; Richard H. Taylor, 13691 Gershon Pl., Santa Ana, Calif. 92705; Richard D. McGunigle, 1135 Picaaho Dr., La Habra Heights, Calif. 90631

[21] Appl. No.: 12,984

[22] Filed: Feb. 21, 1979

[51] Int. Cl.³ .............................................. A61H 1/00
[52] U.S. Cl. .................... 128/24 A; 128/62 A
[58] Field of Search .................... 128/24 A, 62 A, 66; 32/58

[56] References Cited

U.S. PATENT DOCUMENTS

| | | | |
|---|---|---|---|
| 3,584,327 | 6/1971 | Murry | 128/24 A |
| 3,760,799 | 9/1973 | Crowson | 128/24 A |
| 3,809,977 | 5/1974 | Balamuth et al. | 128/62 A |
| 4,144,646 | 3/1979 | Takemoto et al. | 128/24 A |
| 4,148,309 | 4/1979 | Reibel | 128/24 A |

Primary Examiner—Lawrence W. Trapp
Attorney, Agent, or Firm—Nilsson, Robbins, Dalgarn, Berliner, Carson & Wurst

[57] ABSTRACT

A hand-held ultrasonic tooth-cleaning apparatus which may be inserted into the mouth to remove materials from the teeth by cavitation using a lip seal or a continuous liquid flow. Electromechanical transducer elements are used to establish propagation of ultrasonic energy in a transverse mode with respect to the longitudinal axis of a vibrating member one terminus of which constitutes the probe which is inserted into the mouth by the user.

22 Claims, 10 Drawing Figures

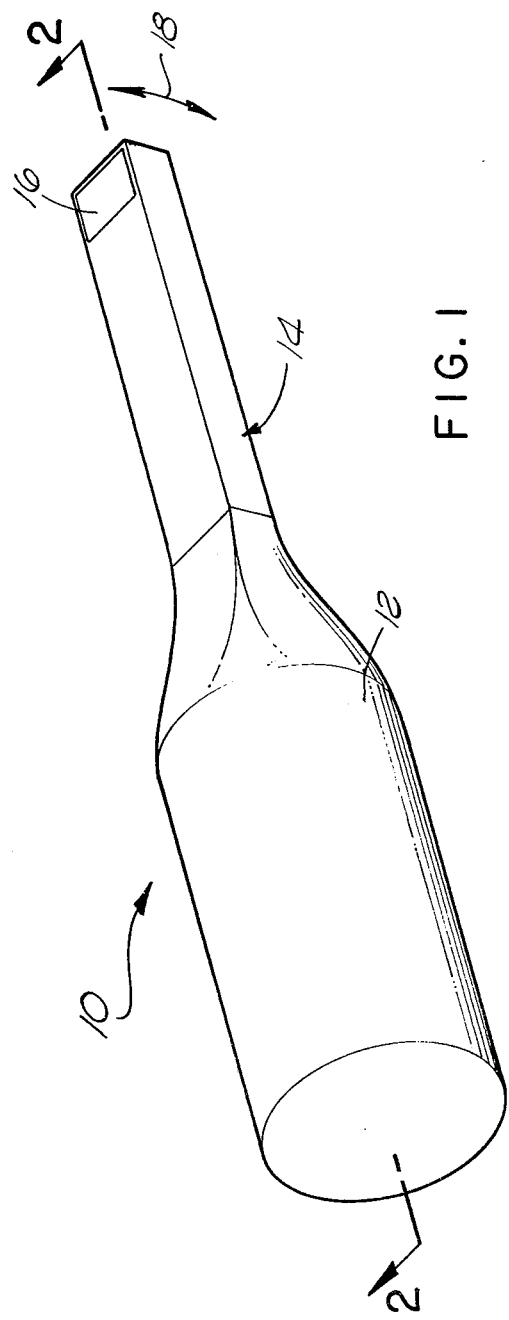
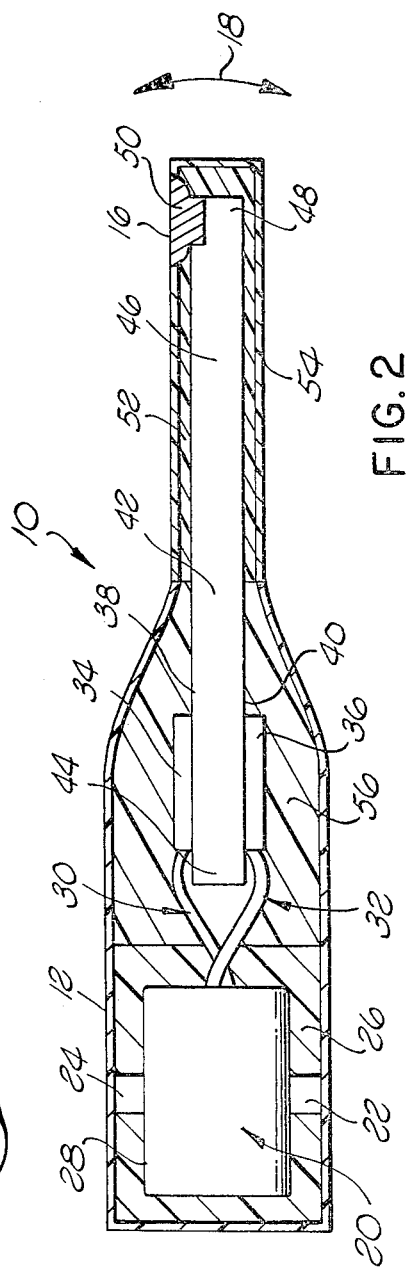
FIG. 1
FIG. 2

ULTRASONIC TOOTH CLEANING APPARATUS

BACKGROUND OF THE INVENTION

It has long been known that the usual means of cleaning teeth, such as by a toothbrush and toothpaste, leaves a great deal to be desired insofar as removing bacteria, plaque, and other foreign matter is concerned. To properly clean teeth, one must in addition use dental floss. With proper use of dental floss employing adequate manual dexterity over sufficient time along with brushing, adequate tooth cleaning can be accomplished. However, it has been well established that most people do not have the required manual dexterity or refuse to spend the amount of time necessary to properly clean their teeth. To solve some of the problems relating to the ineffectiveness of the toothbrush and toothpaste tooth-cleaning means, apparatus applying pulsating water or liquid to the teeth and gums was generated. Although such a device assisted in cleaning the mouth, it was still found not to be effective insofar as matter secured to the teeth is concerned.

Ultrasonic tooth-cleaning apparatus was then invented for use in cleaning the surface of the teeth. This apparatus included the insertion of an ultrasonic generating means into the mouth cavity which had been partly filled with a liquid to serve as a medium for the transmission of sonic energy from the transducer throughout the mouth cavity to the surfaces of the teeth. In addition thereto, ultrasonic energy has also been utilized to vibrate a mechanical member such as a pick or other tool to loosen calculus from the surface of the teeth.

Such prior-art apparatus although somewhat effective either required use by a highly trained person, such as a dentist or hygienist, to preclude damage to the gingival and non-gingival areas of the mouth, or required the insertion into the mouth of the active portions of the ultrasonic generator. In some instances, the ultrasonic radiating surface has been inserted into the mouth of the user in such a manner that the radiated energy is ineffectively applied to the teeth and/or is allowed to impact upon other areas of the mouth and throat wherein some damage could possibly occur.

In all known prior art, ultrasonic dental-cleaning devices where an active element is not directly inserted into the mouth, the ultrasonic energy has been propagated along the vibrating element in a compressional mode. Under such propagation, the ultrasonic energy necessarily emanates from the tip of the member in a direction parallel to the longitudinal axis thereof. With such a device, it becomes extremely cumbersome if not impossible for use by an individual to clean his own teeth. For proper use by an individual upon his own teeth, it becomes necessary to radiate the energy transversely of the longitudinal axis of the vibrating element. To accomplish this in the prior art, the vibrating element along which the acoustical energy is propagated has been fitted with brushes, bent members, and the like. In all of these instances, the affect has been basically to merely provide a mechanical toothbrush/toothpaste-cleaning system. Although more effective than hand brushing, such systems still lacked easy, quick, and safe removal of bacteria, plaque, and other foreign matter from all surfaces of the teeth.

The best prior art known to applicants which illustrate the foregoing devices is disclosed in the following United States patents:

U.S. Pat. Nos. 3,760,799; 3,466,689; 3,401,690; 3,166,772; 3,514,328; 3,427,480; 3,847,662; 3,645,255; 3,380,446; 3,589,012; 2,980,123; 3,526,036; 3,154,890; 3,518,766; 3,522,801; 3,375,583; 3,593,425; 2,990,616; 3,488,788; 3,368,280; 3,703,037; 3,636,947; 3,863,628; 3,547,110; 4,012,842; 3,809,977; 3,375,820; 3,763,411; 3,335,443; 3,956,826.

SUMMARY OF THE INVENTION

A hand-held ultrasonic tooth-cleaning apparatus having a radiating surface to transmit ultrasonic energy from the radiating head to the teeth through a sonic couplant solution to effect cleaning by cavitation action which includes a probe defining a radiating surface disposed substantially parallel to the longitudinal axis thereof. The probe constitutes a portion of a member for receiving ultrasonic energy which is generated by means therefor attached to the member in such a fashion as to propagate the ultrasonic energy through the member in a transverse mode with respect to the longitudinal axis of the body. The radiating surface is positioned at a point on the probe of maximum displacement to maximize the intensity of the acoustic energy at the radiating surface. A coating of low acoustic impedance material is provided over the member except for the radiating surface to substantially reduce the loss of the acoustical energy except at the radiating surface.

In accordance with more detailed aspects of the present invention:

a. the probe portion of the member may be detachably affixed to the body portion thereof so that a plurality of users may employ the same ultrasonic-generating portion of the device with different probes;

b. means for applying a liquid solution in a continuous flow directly to the vicinity of the radiating surface of the probe;

c. spacer means for assisting the user in positioning the radiating surface adjacent the teeth to be cleaned;

d. feedback means to maintain maximum resonance of the member at the radiating surface irrespective of frequency changes therein through variations in loading; and e. timer means to assist the user while cleaning his teeth.

BRIEF DESCRIPTION OF THE DRAWING

FIG. 1 is a perspective view of apparatus constructed in accordance with the present invention;

FIG. 2 is a partial cross-sectional view of the apparatus of FIG. 1 taken about the line 2—2 thereof;

DESCRIPTION OF THE ILLUSTRATIVE EMBODIMENTS

Figure 5:
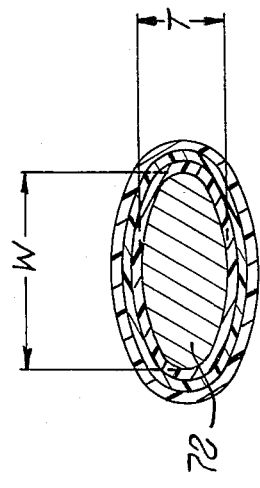
FIG. 5 is a cross-sectional view taken about the line 5—5 of FIG. 4 to show an alternative configuration for a probe constructed in accordance with the principles of the present invention.

As is illustrated particularly in FIG. 1, there is shown a hand-held ultrasonic tooth-cleaning apparatus 10 which includes a housing member 12 and a probe 14 which is insertable into the mouth of a user for cleaning teeth of the user through application of ultrasonic energy. A radiating surface 16 is provided on the probe 14 and it is from the surface 16 which the ultrasonic energy is allowed to radiate.

It will be noted from a consideration of FIG. 1 that the plane of the surface of the radiating surface 16 is substantially parallel to the longitudinal axis of the probe 14. In this manner, the ultrasonic energy is caused to leave the radiating surface in a direction which is perpendicular to the longitudinal axis of the probe 14. By so positioning the radiating surface 16, the user of the apparatus 10 may easily position the radiating surface 16 adjacent the teeth in such a manner that it will be comfortable and convenient for him to do so and in fact will be manipulatable much in the same fashion as a toothbrush which all users are familiar with.

To cause the ultrasonic energy to radiate from the surface 16 positioned in the manner illustrated in FIG. 1, the radiating surface 16 is caused to oscillate in a mode such as illustrated by the arrow 18. That is, ultrasonic energy is propagated through the probe 14 in a mode which is transverse with respect to the longitudinal axis of the probe 14. It is through the utilization of such transverse mode propagation that a simple, ultrasonic tooth-cleaning apparatus utilizable by any user without special training or assistance is possible. Various attempts have been made in the prior art to provide such radiation through the techniques of turning the ultrasonic energy generated in the compressional mode so as to emanate in a direction transverse to the longitudinal axis of the probe. It has not previously been recognized that through propagation of the ultrasonic energy in the transverse mode and by positioning the radiating surface at an appropriate point on the probe, that sufficient intensity and radiation of the energy would be obtainable with a hand-held unit usable by any person without special training or skill. Thus, there has been achieved an unexpected and unusual synergistic affect by way of constructing the apparatus 10 in accordance with the principles of the present invention.

It will be recognized by those skilled in the art that the apparatus shown in FIG. 1 is designed basically for home use by an untrained person. In using the apparatus of FIG. 1, the user would place an appropriate amount of sonic coupling liquid such as water or a desired cleaning solution in his mouth and thereafter insert the probe 14 through his closed lips which function as a seal to retain the liquid in the user's mouth. Ultrasonic energy is generated and cavitation is commenced and maintained adjacent the teeth surfaces to fully and completely clean all surfaces thereof even in hard-to-reach interproximal areas. Obviously, the apparatus may also be adequate for use by a dentist or other trained person as will be more fully discussed later.

By reference now to FIG. 2, the apparatus 10 of FIG. 1 is illustrated in partial cross-section thereby disclosing further details thereof. As is therein illustrated, a source of energizing potential 20 is supported within the housing 12 by any means desired such, for example, as by utilizing supporting ribs 22–24 or by a plastic foam 26, or a combination thereof which hold a casing 28 in position within the housing 12.

It will be recognized that the source of potential may also be external to the housing 12 and provided, for example, by plugging into a standard wall socket with cord 20A while the source 20 internally of the housing would be a typical converter circuit known to those skilled in the art. Such a unit would typically be employed by a dentist.

Internally of the casing 28, there would also be disposed an oscillator and appropriate control circuits for providing energizing potential over the leads 30 and 32 to the ultrasonic generating means including transducers 34 and 36 such, for example, as a polarized ceramic, for example, lead zirconate-titanate. Although a pair of transducers are shown it will be understood that a single transducer or more than two transducers may be used if desired. Obviously, alternative materials may be utilized to generate the ultrasonic energies such as piezoelectric crystal, magnetostrictive nickel, or other suitable materials which will operate at suitable cleaning frequencies on the order of 15–100 kilohertz.

In accordance with the principles of the present invention, the ultrasonic generators 34 and 36 are permanently bonded to opposed surfaces 38 and 40 respectively of the ultrasonic vibrating member 42. The member 42 includes a body portion 44 and a probe portion 46. The ultrasonic generating members 34 and 36 are caused to vibrate in opposite phase relationship through application of the energizing energy thereto in such a manner that the member 42 effectively is caused to bend about points along the longitudinal axis thereof. The members 34 and 36 are positioned such that they are effectively at an anti-nodal position along the member 42 when the resonant frequency thereof is ascertained. By so placing the members 34 and 36 and by properly orienting and exciting them, the members 34 and 36 vibrate out of phase with respect to each other, causing the member 14 to bend thus setting up vibrations therein. These vibrations will cause energy at ultrasonic frequencies to be propagated along the member 42 in a transverse mode with respect to the longitudinal axis thereof. To more fully explain, upon excitation of the member 34, it will flex in such a manner that the outer surface thereof will be convex and at the same time the outer surface of the member 36 will be concave. By outer surface in each instance is meant the surface which is not secured to the member 42. It will thus be seen that by such "bending" of the members 34 and 36, the ultrasonic member 42 is caused to bend likewise. By causing the bending to occur at the resonant frequency of the member or rod 42, vibrations may be generated and sustained therealong.

By choosing the length of the rod 42 appropriately, the end 48 thereof may be selected to be at an anti-mode thereby maximizing the intensity of the ultrasonic energy present at that point. By positioning the radiating surface 16 at that point, ultrasonic energy is caused to leave the surface 16 with maximum intensity. It will be noted that the radiating surface 16 may be formed from an insert 50 which is bonded to the probe portion 46 of the rod 42 so as to be permanently attached thereto. By utilizing such an insert 50, the shape of the radiating surface 16 may be tailored as desired. Typically, the radiating surface 16 is chosen to have an area sufficient to cover at least one tooth of an average adult human being. By so doing, the energy radiating from the surface 16 may be applied through a couplant solution (as will be more fully discussed hereinafter) to set up cavitation therein upon the surface of the teeth and in the interproximal areas thereof to thus effectively and efficiently loosen and remove the bacteria, plaque, and other foreign matter therefrom through the utilization of the cavitation caused by the ultrasonic energy.

As will be recognized by those skilled in the art, vibration of the rod 42, as above described, would normally cause energy in ultrasonic frequencies to be radiated from the upper and lower surfaces 38 and 40 thereof. To preclude such radiation except from the desired radiating surface 16, the rod 42 is enclosed in a low acoustic impedance material 52 such as a polyurethane foam, Corprene, or the like. Such material effectively provides a layer of air around the rod 42 thus preventing radiation of ultrasonic energy from those surfaces coated with the material 52. Since the probe portion 46 of the rod 42 will be inserted into the mouth, which will contain liquids, it is believed desirable to provide the outer surface of the material 52 with a skin 54 which is preferably waterproof and yet would be pleasant insofar as a sense of touch or feeling is concerned to the user. The material 52 may be chosen from castable polyurethane foams which may be cast in place around the probe portion 46 of the rod 42. Through utilization of such castable materials, any exterior geometric configuration desired may be provided for the probe. The skin 54 may also be chosen from any type of material desired, such as silicone or epoxy, and known to those skilled in the art which will adhere to the surface of the material 52 and provide a waterproof coating which is pliable.

The body portion 44 of the rod 42 is also covered with a low acoustic impedance material 56, such as any open-cell foam material such as again a polyurethane foam, and functions to prevent radiation of the ultrasonic energy from the rod 42. The housing 12 may in turn be constructed of appropriate plastic material, such as polyethylene or polyvinyl chloride, within which the source 20 and the body portion 44 of the rod 42 may be housed and properly supported.

Figure 3:
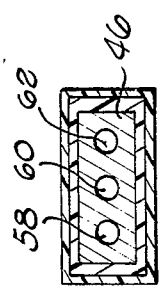
FIG. 3 is a cross-sectional view taken about the line 3—3 of FIG. 1 to illustrate one form of the probe of the apparatus constructed in accordance with the present invention.

The rod 42 may be tailored to assist in providing the desired frequency of vibration thereof. Such may be accomplished as is illustrated in FIG. 3, for example, by defining openings 58, 60, and 62 therein. As will be recognized by those skilled in the art, by so relieving the rod 42 or portions thereof, the mass to stiffness ratio may be altered and the resonant frequency of the rod may be changed or tailored to the desired frequency for the particular length of the probe portion 46 desired in any given application.

Although the rod 42 is illustrated as being rectangular such is a schematic illustration only. The rod may be contoured or shaped along its length to any desired geometric configuration.

Figure 4:
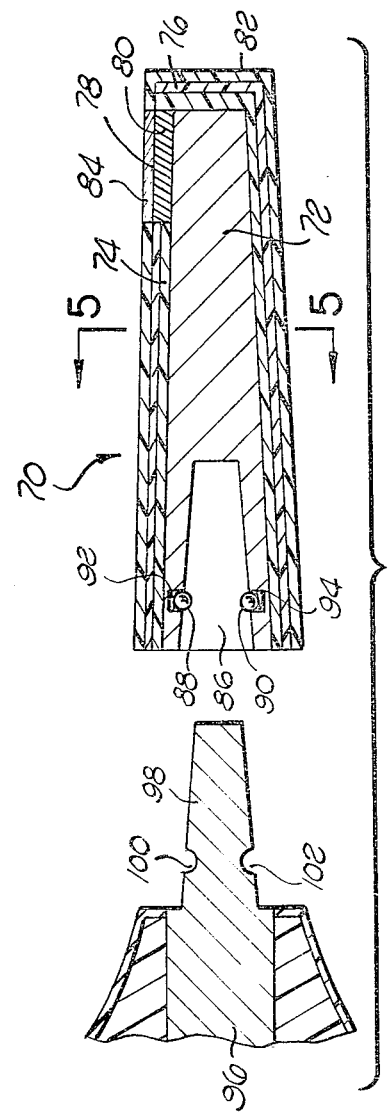
FIG. 4 is a partial cross-sectional view (exploded) showing an alternative embodiment of apparatus constructed in accordance with the principles of the present invention.

Those using the ultrasonic tooth-cleaning apparatus constructed in accordance with the principles of the present invention in the home may desire to have different probes 14 for each member of a family all usable with the same housing 12. Such a structure is schematically illustrated in FIG. 4 to which reference is hereby made. As is therein shown, a probe 70 includes a probe portion 72 which is coated with the low acoustic impedance material 74 and a waterproofing layer 76 thereover. A radiating surface 78 is provided in the form of a plate 80 which is bonded permanently to the upper end surface of the probe portion 72.

In the event the same probe portion would be utilized by various persons, a sleeve 82 may be provided and constructed of a material such, for example, as polyethylene or the like, which is slipped over the outer waterproofing layer 76. With such a unit a section 84 must be provided in the form of an acoustic window through which the acoustic radiation may pass without interference.

The probe portion 72 defines an opening 86 within which there are secured detent means in the form of balls 88 and 90 which are spring loaded into the recesses 92 and 94 respectively. The body portion 96 includes a tongue 98 which is received within the opening 86 and conforms thereto. Depressions 100 and 102 are formed on opposite sides of the tongue 98 and receive the balls 88 and 90 thereby providing a detent-type locking mechanism so that when the probe portion 72 is seated upon the body portion 96, it may be secured in place to thereby provide a completed rod which transmits the ultrasonic energy from the generators thereof to the radiating surface 78 in the transverse mode with respect to the longitudinal axis of the probe 70 and the body 96.

As is illustrated in FIG. 5 to which reference is now made, the probe portion 72 may have an oval configuration. As will be noted by comparison to FIG. 3, the probe portion 46 is rectangular in configuration. Any desired geometric configuration may be utilized so long as the width dimension W is greater than the thickness dimension T by an amount sufficient to prevent the rod from vibrating in a direction orthogonal to that shown by the arrow 18 (FIGS. 1 and 2). A ratio of approximately 1.5 to 1 of width to thickness is sufficient to preclude such an occurrence.

With the structure as thus far illustrated and above described, the user thereof would place a liquid couplant solution containing, if desired, appropriate cleaning material or mouthwash into his mouth. Thereafter, the probe 14 would be inserted into the mouth adjacent the teeth in such a manner that it was immersed in the liquid couplant. Thereafter, the transducers 34 and 36 would be energized by activating an appropriate switch (not shown) located on the housing to cause the ultrasonic energy to radiate from the surface 16. By placing the radiating surface 16 adjacent the teeth, the liquid couplant is caused to cavitate since there is a direct acoustic coupling of the radiating surface 16 and the liquid couplant solution. This cavitation created by the ultrasonic energy through the formation and collapse of bubbles in the liquid solution against the surface of the teeth causes a breaking up of the bacteria, plaque, and other foreign matter which may be present on the surface of teeth. With such a structure operating in the manner as just described, the probe 14 may be constructed in such a manner that there is a reduced area portion thereof displaced from the radiating surface 16 to assist the user in positioning the radiating surface 16 and in maintaining a lip seal about the probe 14.

Figure 6:
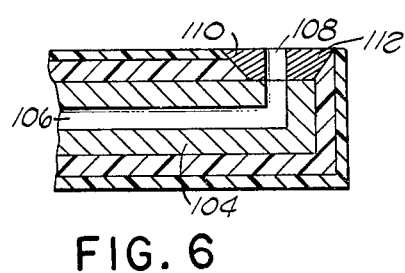
FIGS. 6 and 7 are fragmentary cross-sectional views illustrating alternative embodiments of probes constructed in accordance with the principles of the present invention wherein liquid is applied to the radiating surface of the probe.
Figure 7:
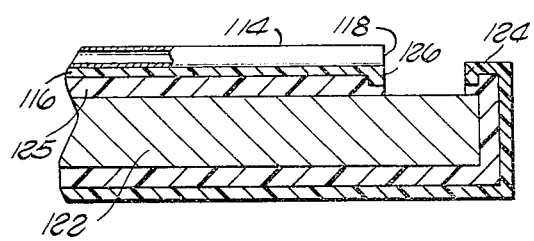

Under some operating conditions, particularly when the device is being used by a dentist, it may be desired to transport the liquid couplant through or along the probe and into contact in a continuous flowing manner with the surface of the teeth. In such cases no lip seal is required and excess liquid in the patient's mouth would be removed by an aspirator. This same device may also be used by the home user and the user would simply position his mouth over a sink to catch and dispose of the liquid as it flows from the mouth. Alternative embodiments for providing such an operation are illustrated in FIGS. 6 and 7 to which reference is hereby made. As is shown in FIG. 6, a probe 104 defines an opening 106 through the interior thereof. The opening terminates at orifice 108 in the radiating surface 110. The radiating surface 110 is defined by a button-like member 112 having an enlarged outer surface with the smaller inner surface being affixed to the probe 104 in a permanent manner. With such a structure, the liquid couplant would be caused to flow through the opening 106 and out the orifice 108 against the teeth in a volume sufficient to provide adequate liquid couplant to support cavitation adjacent the teeth. If such is desired, one may flow fluid through a multiplicity of conduits provided in the probe as is illustrated in FIG. 3.

Alternatively, as shown in FIG. 7, a separate conduit 114 may be affixed to the outer layer 116 of waterproofing material with the orifice 118 terminating adjacent the radiating surface 120. It will be noted that the radiating surface 120 is formed by the upper surface of the probe portion 122 without any addition of other materials. If desired, a pair of spacer or locating members 124 and 126 may be formed on the surface of the probe portion 122 adjacent the radiating surface 120 to assist the user in appropriately positioning the radiating surface 120 with respect to the surface of the teeth. The members 124 and 126 are preferably formed as part of the isolating foam layer 125 and the protective film 116 as shown. In this manner, the user will always feel comfortable in that the radiating surface 22 will never directly engage the teeth and the user, by holding the spacers 124 and 126 against or closely adjacent the teeth, will always know that the spacing is appropriate to maintain effective cavitation at all times. Obviously, the spacers 124 and 126 may be utilized with any of the radiating surfaces previously disclosed and above described.

Figure 8:
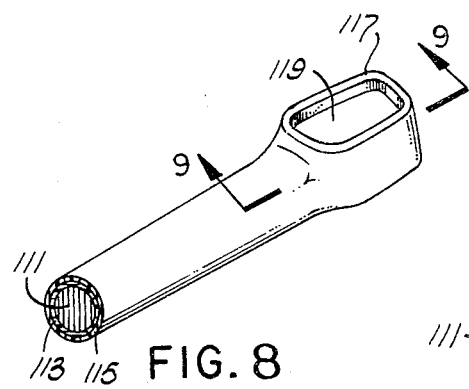
FIG. 8 is a fragmentary perspective view illustrating an alternative construction for a probe.
Figure 9:
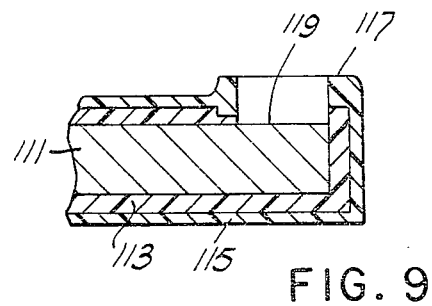
FIG. 9 is a fragmentary cross sectional view of the structure of FIG. 8 taken about the lines 9—9 of FIG. 8.

In FIGS. 8 and 9 there is disclosed an alternative configuration and spacing or locating structure. As is therein illustrated, a rod 111 is surrounded by an isolating foam layer 113 around which is cast a film layer 115. As shown at 117 the foam and film are formed as a cup around the radiating surface 119. Such provides an effective barrier between the teeth and the radiating surface 119. It is not thought such a barrier is necessary, but the user may feel more comfortable particularly at lower frequencies of operation in having such a spacer or locating structure present.

Figure 10:
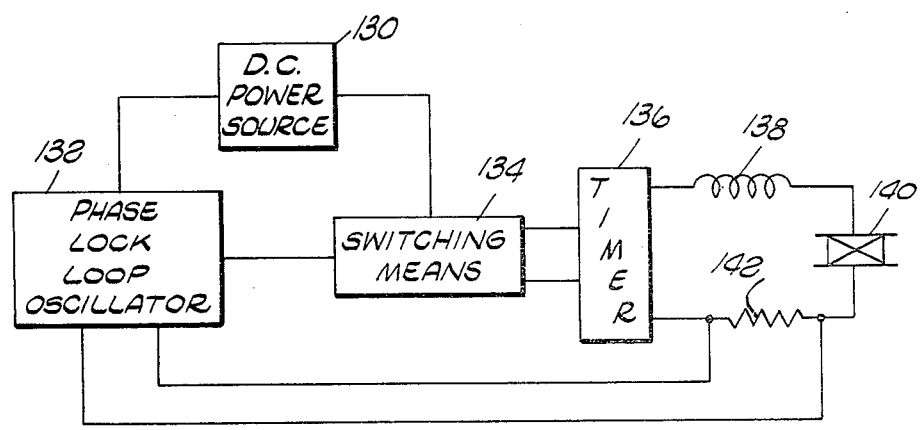
FIG. 10 is a schematic diagram illustrating the circuit for applying energizing potential to the transducers affixed to the ultrasonic vibrating member of the present invention.

Referring now more particularly to FIG. 10, there is disclosed a schematic diagram of the circuit utilized to energize the ultrasonic generators or transducers 34 and 36. As above described, the circuit as shown in FIG. 10 will be housed within the casing 20 disposed within the housing 12. There is provided a direct current power source 130 such, for example, as a rechargeable battery currently readily available. A phase-lock loop oscillator 132 is provided and is connected to a switching means 134 such, for example, as a straightforward converter circuit. The output of the phase-lock loop oscillator would be used to provide a clock at the desired frequency to the switching means 134. The switching means 134 would apply the output of the DC power source 130 therethrough to a timer circuit 136 and thus through an appropriate inductance 138 to the ultrasonic generator means such as the polarized ceramic 140 or the like. The particular phasing of the energy applied to the member 140 is chosen to provide a maximum resonance of the vibrating rod at the radiating surface. That phasing is sensed through the sensing resistor 142 and applied to the phase-lock loop oscillator 132 to cause it to always function at the desired phase irrespective of current or frequency changes which may occur as a result of changes in the loading of the probe at the radiating surface such, for example, by the spacing with respect to the teeth, application of more or less liquid couplant, and the like. Through the utilization of this technique, maximum intensity of radiation is always maintained at the radiating surface.

The timer means 36 may function in several ways. The timer means 36 may be programmed to provide a specified amount of time during which the user may clean his teeth. This predetermined time would be chosen commensurate with appropriate health parameters in mind. In addition, the timer means may also be programmed to provide an appropriate signal, audible or otherwise, to the user indicating that he should move the radiating surface from where it is to an adjacent tooth area because sufficient time has elapsed to clean the surface of the teeth against which the radiating surface has been held for the preceding time interval. An additional utilization of the timer means 36 is to provide energizing energy to the ultrasonic generator means 140 intermittently. By so doing, for example on the order of 40 or 50 times per second, cavitation may be enhanced in that the cavitation bubbles will be allowed to dissipate before generation of additional ones.

In those embodiments of the present invention adapted for use by a dentist or other trained personnel, it will be recognized that the power source and control circuit may be housed remotely from the vibrating element.

From a consideration of the foregoing structures, it will be recognized by those skilled in the art that the conjunction of the housing member 12 with the sheath or coating on the probe portion 46 should be at a nodal point along the rod 42. By selecting the nodal point for such to occur, there will be less likelihood of damage or wear to the structures at this point. Similarly, when a removable probe such as that shown at 70 in FIG. 3 is used, the interconnection between the removable probe and the body should also be positioned at a nodal point to minimize interference with the propagation of the ultrasonic energy along the vibrating member.

As will be recognized by those skilled in the art, the ultrasonic vibrating member, such as the rod 42, may be constructed of any material desired so long as the ultrasonic vibrations are maintained within the stress limits of the material and within the temperature limits of the material. In accordance with the preferred embodiment of the present invention, the rod 42 would be constructed of aluminum or stainless steel with the structure from which the radiating surfaces are formed constructed of the same or similar materials.

What is claimed is:

1. A hand-held ultrasonic tooth-cleaning apparatus having a radiating surface for insertion into an oral cavity to transmit ultrasonic energy from the radiating head to the teeth through a liquid sonic couplant to effect cleaning by cavitation action, said apparatus comprising:
- A. a vibrating member including:
  1. a body member;
  2. a probe coupled to said body member;
     (a) said probe defining a radiating surface disposed substantially parallel to the longitudinal axis of said vibrating member;
- B. means disposed externally of the mouth for generating ultrasonic energy at a frequency and amplitude sufficient to establish cavitation within said liquid couplant adjacent said teeth; and
- C. means for attaching said ultrasonic generator means to said vibrating member for establishing propagation of ultrasonic energy in said body and said probe in a transverse mode with respect to the longitudinal axis of said body and said probe said radiating surface being positioned at a point of maximum displacement on said probe to maximize the intensity of acoustic energy at said radiating surface.

2. The hand held ultrasonic tooth-cleaning apparatus defined in claim 1 further including low acoustic impedance means on said body and said probe except for said radiating surface to substantially reduce the loss of acoustical energy from said body and said probe except through said radiating surface.

3. The hand-held ultrasonic tooth-cleaning apparatus as defined in claim 2 which further includes a waterproof sheath over said low acoustic impedance means.

4. The hand-held ultrasonic tooth-cleaning apparatus as defined in claim 1 wherein said radiating surface is a smooth, unbroken surface.

5. The hand-held ultrasonic tooth-cleaning apparatus as defined in claim 4 which further includes spacer means displaced from said radiating surface for maintaining said surface spaced from said teeth.

6. The hand-held ultrasonic tooth-cleaning apparatus as defined in claim 1 which further includes timing means for automatically de-energizing said means for generating acoustic energy after a predetermined period of time.

7. The hand-held ultrasonic tooth-cleaning apparatus as defined in claim 1 wherein said probe and said body are formed from a unitary metallic member and said probe includes a smaller transverse cross-sectional area than said body.

8. The hand-held ultrasonic tooth-cleaning apparatus as defined in claim 1 which further includes housing means and means for securing said body and said means for generating ultrasonic energy within said housing means.

9. The hand-held ultrasonic tooth-cleaning apparatus as defined in claim 1 wherein said radiating surface is configured to have a length and width sufficient to cover at least one tooth of an average adult human being.

10. The hand-held ultrasonic tooth-cleaning apparatus as defined in claim 1 which further includes means for intermittently energizing said means for generating at a predetermined repetition rate sufficiently low enough to permit cavitation bubbles to dissipate and increase the efficiency of said apparatus.

11. The hand-held ultrasonic tooth-cleaning apparatus as defined in claim 1 which further includes an interval timer means for providing a signal to the user of said apparatus to move said radiating head from one position to another position within the mouth.

12. The hand-held ultrasonic tooth-cleaning apparatus as defined in claim 1 wherein said probe is removably coupled to said body member at a nodal point with respect to the frequency of vibration of said member.

13. The hand-held ultrasonic tooth-cleaning apparatus as defined in claim 1 wherein said probe defines an opening therein.

14. The hand-held ultrasonic tooth-cleaning apparatus as defined in claim 13 which further includes means defining an orifice in said radiating surface communicating with said opening in said probe for applying liquid through said opening and through said orifice.

15. The hand-held ultrasonic tooth-cleaning apparatus as defined in claim 14 wherein said probe defines a plurality of openings for providing liquid to said orifice.

16. The hand-held ultrasonic tooth-cleaning apparatus as defined in claim 1 which further includes conduit means defining an orifice, said orifice being positioned at said radiating surface for applying liquid couplant to said radiating surface.

17. The hand-held ultrasonic tooth-cleaning apparatus as defined in claim 1 in which said probe defines an elliptical cross-section.

18. The hand-held ultrasonic tooth-cleaning apparatus as defined in claim 1 in which said probe defines a rectangular cross-section.

19. The hand-held ultrasonic tooth-cleaning apparatus as defined in claim 1 wherein said means for generating ultrasonic energy includes means for detecting the phase of oscillation and for maintaining the same at a predetermined phase to maximize the resonance of the member at said radiating surface.

20. The hand-held ultrasonic tooth-cleaning apparatus as defined in claim 19 wherein said means for generating ultrasonic energy further includes switching means, a source of direct current potential coupled to said switching means, a phase-lock loop oscillator coupled to said switching means, said switching means passing potential from said source of direct current potential in response to signals received from said phase-lock loop oscillator.

21. The hand-held ultrasonic tooth-cleaning apparatus as defined in claim 1 which further includes spacer means providing a surface spaced from said radiating surface to preclude direct contact of a tooth with said radiating surface.

22. The hand-held ultrasonic tooth-cleaning apparatus of claim 21 wherein said spacer means provides a continuous surface surrounding said periphery of said radiating surface.

* * * * *